United States Patent [19]
Dittmer et al.

[11] Patent Number: 5,087,773
[45] Date of Patent: Feb. 11, 1992

[54] SELECTIVE TELLURIUM-MEDIATED SYNTHESIS OF OPTICALLY ACTIVE E- OR Z-ALLYL ALCOHOLS FROM OPTICALLY ACTIVE EPOXY ALCOHOLS

[75] Inventors: Donald C. Dittmer; Christopher K. Murphy; Robert Discordia, all of Syracuse, N.Y.

[73] Assignee: Syracuse University, Syracuse, N.Y.

[21] Appl. No.: 512,863

[22] Filed: Apr. 23, 1990

[51] Int. Cl.$^5$ .................... C07C 29/00; C07C 33/03; C07C 33/14
[52] U.S. Cl. .................... 568/828; 568/908
[58] Field of Search ................ 568/908, 828

[56] References Cited

U.S. PATENT DOCUMENTS

| | | | |
|---|---|---|---|
| 3,673,264 | 6/1972 | Kuhn | 260/633 |
| 4,069,385 | 1/1978 | Araki et al. | 568/106 |
| 4,471,130 | 9/1984 | Katsuki et al. | 549/523 |
| 4,594,439 | 6/1986 | Katsuki et al. | 549/523 |
| 4,935,451 | 6/1990 | Dittmer et al. | 568/908 |
| 5,004,843 | 4/1991 | Tamura et al. | 568/828 |

FOREIGN PATENT DOCUMENTS

| | | |
|---|---|---|
| 29603 | 6/1981 | European Pat. Off. . |
| 157307 | 12/1975 | Japan . |
| 164129 | 12/1981 | Japan . |
| 11930 | 1/1982 | Japan ................ 568/908 |

OTHER PUBLICATIONS

Polson et al. Functional Group Modification via Organotellurium Chemistry Tetrahedron Letters, V. 27, p. 5579 (1986).
Discordia et al., 2—Substituted 4 Hydroxymethyl Tellurophenes, Tetrahedron Letters, V.29, p. 4923.
Barton et al., Sodium Hydrogen Telluride as a Useful Nucleophilic Reagent, Tetrahedron Letters, V.26, p. 6197.
Clive et al. Alkali Metal O, O–Diethyl Phosphorotelluroates, 45J Org. Chemistry 2347 (1980).
Polson et al., Some New 3–Substituted 3–Hydroxyselenetanes, 53J. Org. Chemistry 791 (1988).
Chiral Drug Analysis, Chemical & Engineering News, Mar. 19, 1990, p. 38 to 44.

*Primary Examiner*—J. E. Evans
*Attorney, Agent, or Firm*—Wall and Roehrig

[57] ABSTRACT

Threo- and erythro- epoxy alcohols are converted in high yield to trans- and cis-allyl alcohols, respectively. The threo epoxy alcohol or erythro-epoxy alcohol is reacted with a toluenesulfonic anhydride to form a threo- or erythro- glycidyl tosylate. The glycidyl tosylate is contacted with tellurium ion, in the form, e.g. of Na$_2$Te that has been prepared by adding tellurium in elemental form and sodium borohydride or lithium triethyl borohydride to dimethylformamide (DMF). The DMF has a low volatility and permits further work to be carried out at elevated temperatures. The glycidyl tosylate is added to the sodium telluride in DMF, and is permitted to react. The tellurium ion displaces the tosylate and opens the epoxide to form an unstable alkoxy epitelluride. This epitelluride is a short-lived intermediate, and extrudes the tellurium, leaving the olefin. The opening of the epoxide required the adoption of an anti configuration. Consequently, erythro starting compounds yield cis-allyl alcohols exclusively; threo starting compounds yield trans-allyl alcohols exclusively. If the starting compounds are optically active, the products are also optically active.

8 Claims, No Drawings

SELECTIVE TELLURIUM-MEDIATED SYNTHESIS OF OPTICALLY ACTIVE E- OR Z-ALLYL ALCOHOLS FROM OPTICALLY ACTIVE EPOXY ALCOHOLS

BACKGROUND OF THE INVENTION

The usefulness of many pharmaceutical and agricultural chemicals and other biologically active agents, such as insect pheromones, depends critically on the fact that the molecules have a chiral atom of one specific chirality. However, usual commercial synthesis of these compounds produces a racemic mixture of the product compound, with half the product of the desired chirality, and half of the opposite chirality. That is, when achiral molecules are resolved, two enantiomers are separated per chiral atom, each of opposite chirality. In commercial synthesis processes that utilize chiral allyl alcohols, the molecules whose chirality is opposite to that desired may be of no use, and in some cases can be detrimental.

In a procedure described in Katsuki et al. U.S. Pat. Nos. 4,471,130 and 4,594,439, secondary allyl alcohols are converted from a racemic mixture to a single enantiomer of the desired chirality. This process is called Sharpless Kinetic Resolution (SKR). The enantiomer of the opposite chirality is converted to an epoxy alcohol whose carbinol carbon atom has the opposite configuration. This produces a substantially pure yield of the desired enantiomer of the allyl alcohol, which amounts to about 50% of the racemic mixture. The other enantiomer, converted to an epoxy alcohol, may be of little value in the synthesis of a specific pheromone or other biological agent.

A procedure for converting the chiral epoxy alcohol that results from the SKR process is discussed in copending U.S. patent application Ser. No. 405,684, filed Sept. 11, 1989, now U.S. Pat. No. 4,935,451. This is a two stage process. The racemic allyl alcohols are kinetically resolved by means of the Sharpless Katsuki process in the presence of a titanium alkoxide or equivalent catalyst. This selectively epoxidizes the enantiomer of the undesired chirality and leaves the allyl alcohol of the desired chirality substantially unreacted. The epoxy alcohol and the allyl alcohol can be physically separated.

The undesired epoxide that results from this reaction is converted back to the allyl alcohol, but with its chiral center inverted to the desired chirality. The epoxy alcohol is converted to an epoxy mesylate or tosylate by action of a methanesulfonic anhydride or a toluenesulfonic anhydride in methylene chloride or other suitable carrier, in which pyridine is present. The resulting epoxy mesylate or tosylate is then converted to the allyl alcohol of the desired chirality by contacting it with tellurium ions, e.g. in the form of an aqueous solution of sodium telluride. By action of the tellurium ions the chiral center is inverted, so that the product allyl alcohol has the same chirality as the alcohol produced by kinetic resolution as practiced above. The efficiency of the synthesis of the desired enantiomer is improved by substantially 100% over the Sharpless Kinetic Resolution alone.

The above technique employing tellurium attack of optically pure secondary glycidyl mesylates is limited to those having a terminal epoxide. The glycidyl mesylates that possess internal epoxides i.e., that are vicinally disubstituted react sluggishly or not at all to this treatment by telluride ion. Therefore, the technique described above was more or less limited to one class of epoxides.

Another problem in this field is that it has been difficult to produce optically active olefins or tertiary allylic or optically active cis-allylic alcohols that have a desired relative diastereomer configuration, i.e., by the SKR technique. Stereospecific cis- or trans- olefins are also useful in producing biologically active agents.

OBJECTS AND SUMMARY OF THE INVENTION

It is an object of this invention to convert epoxy alcohols with internal epoxides to optically pure (E) or (Z) allylic alcohols of a single desired chirality.

It is another object to provide a simple and straightforward technique to convert epoxy alcohols which have an internal epoxide to tertiary and secondary allylbic alcohols in high optical purity and whose chiral centers have an undesired chirality to allyl alcohols of the desired chirality.

It is another object of this invention to convert cis- or trans- allyl alcohols, as desired, converted in high yield from glycidyl sulfonates that have a predetermined relative stereochemistry, i.e., threo or erythro.

In accordance with an aspect of this invention, a threo or erythro epoxy alcohol is reacted with a toluenesulfonic anhydride or chloride to form a threo or erythro glycidyl tosylate. The glycidyl tosylate is separated, and is contacted with tellurium ions, in the form e.g. of $Na_2Te$ that has been prepared by adding tellurium in elemental form and sodium borohydride to dimethylformamide (DMF). The DMF has a low volatility and permits further work to be carried out at elevated temperatures. The glycidyl tosylate is added to the sodium telluride in DMF, and is permitted to react. The tellurium ion appears to displace the tosylate and opens the epoxide to form an unstable alkoxy epitelluride. This epitelluride is a short-lived intermediate, and extrudes the elemental tellurium, leaving the olefin. The opening of the epoxides involves $S_N2$ attack by the telluride ion, so the telluride ion and the epoxide adopt an anti configuration. Therefore, erythro starting compounds yield cis-allyl alcohols exclusively, and threo starting compounds yield trans-allyl alcohols exclusively.

This means that a trans -1,2 - disubstituted allyl alcohol can be converted via the Sharpless - Katsuki procedure to an optically active erythro glycidol and thence, by conversion to a tosylate or mesylate and treatment with telluride ion, to an optically active cis -1,2- disubstituted allyl alcohol. This type of product compound can be obtained only in low yield and low optical purity by the Sharpless-Katsuki process starting from a cis-1,2- disubstituted allyl alcohol. Since trans-allyl alcohols are generally more available than are the cis - allyl alcohols, and since the relative rates of epoxidation of the two trans- enantiomers differ more greatly than do those of the cis-enantiomers, the telluride process described above significantly improves the yield and percent enantiomeric excess of chiral cis-allyl alcohols.

In this process the reducing system and solvent involve tellurium reduced by sodium borohydride in dimethylformamide. This produces sodium telluride, diborane, and hydrogen gas. Very little is known about this system. However, it is believed that the sodium telluride and diborane may form a complex that assists in the attack of the epoxide by coordinating with the epoxide oxygen. This may increase the positive charge at the epoxide carbons and facilitate attack by telluride ions.

The above and many other objects, features, and advantages of this invention will become more fully apparent from ensuing description of a preferred embodiment.

DETAILED DESCRIPTION OF THE PREFERRED EMBODIMENTS

Many principles leading to this invention are found in copending U.S. patent application Ser. No. 405,684, filed Sept. 11, 1989, now U.S. Pat. No. 4,935,451 also assigned to Syracuse University. The disclosure therein is incorporated here by reference. According to the procedures disclosed therein, optically pure glycidyl sulfonates having terminal epoxides are produced with methanesulfonic acid anhydride (MsAA) and pyridine, and converted in high yield to optically pure allyl alcohols by the action of sodium telluride in aqueous basic solution.

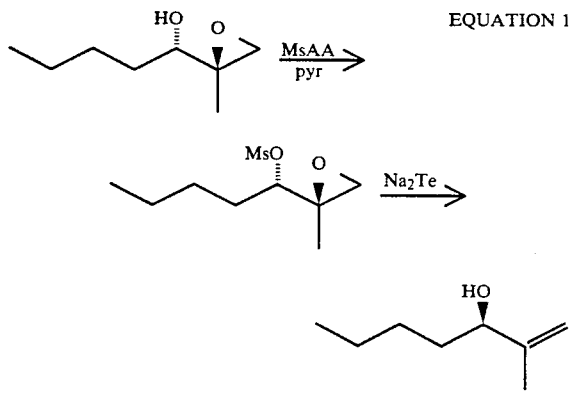

EQUATION 1

Here, the chirality is indicated by the convention of wedges and broken lines, where solid straight lines are considered in the plane of the paper, wedges indicate that the attached group is in front of the plane of the paper, and a broken line indicates that the attached group is behind the plane of the paper. Wavy lines indicate a mixture of each chirality. As is also conventional, carbons are assumed at the nodes of the formulas, and hydrogens are omitted from the formulas.

The mechanism that best describes the observed reactivity is one in which telluride ion, generated by the reduction of elemental tellurium by sodium hydroxymethanesulfinate (Rongalite), attacks the terminal end of the epoxide. The resulting alkoxy-telluride compound forms another epoxide by the internal displacement of the sulfonate group causing this center to be inverted. The olefin is produced by the extrusion of tellurium which causes the opening of the newly formed epoxide to give the optically pure allyl alcohol.

Unfortunately, the above process appears to be limited to species that possess terminal epoxides geminally substituted, because glycidyl mesylates possessing internal epoxide vicinally substituted did not respond to contact with telluride ion.

We have discovered a new set of reaction conditions which circumvent this problem and permit species that possess internal epoxides to be converted to optically pure allyl alcohols. A principal change was made to our previous reaction system. This change involved the reduction of the Te by NaBH$_4$ instead of by sodium hydroxymethane sulfinate. The leaving group also was changed to toluenesulfonate.

In this case where a sulfonate leaving group is used, e.g. toluenesulfonyl, TsO$^-$, the glycidyl toluenesulfonates (tosylates) with internal epoxides were selectively attacked at the carbon bearing the sulfonate center to produce an allyl alcohol that was isomeric with respect to the allyl alcohol from which the starting glycidyl sulfonate was derived. That is, when glycidyl tosylates which possess threo stereochemistry are reacted with telluride ions, trans-allyl alcohols are produced. Conversely, when erythro glycidyl tosylates are reacted with the telluride ions, cis-allyl alcohols are produced. These processes yield their respective products exclusively, so that an optically pure threo epoxide will yield an optically pure trans allyl alcohol exclusively, and an optically pure erythro epoxide will yield an optically pure cis allyl alcohol exclusively, as indicated in equations 2 and 3. As is apparent from Table I and II below, R$_1$ can be hydrogen, normal lower alkyl, allyl and cyclohexyl, and R$_2$ can be normal lower alkyl and cyclohexyl.

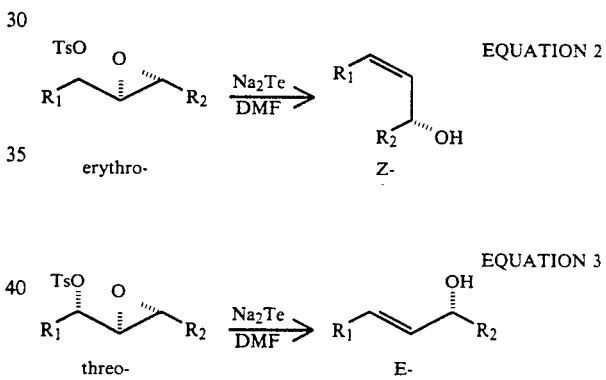

Tosylation is accomplished, e.g. with p-toluenesulfonic anhydride in pyridine.

If diastereotopically pure erythro tosylate is subjected to treatment with telluride ion, the only observed product is the cis-allyl alcohol. Likewise, pure threo tosylate yields only the trans-allyl alcohol. In this reaction the telluride ion appears to displace the tosylate to produce an intermediate organotelluride. It is believed that the tellurium atom, which bears a negative charge opens the epoxide intramolecularly to form an alkoxy-epitelluride. The unstable epitelluride readily discharges tellurium as the element, to form the olefin. Because the opening of the epoxide of the organotelluride is due to an S$_N$2 process, the telluride ion and the epoxide must assume an anti configuration. For erythro compounds, this involves a rotation of the carbon group containing the epoxide, and results in a cis- (Z-) allyl alcohol. For threo compounds, the telluride and epoxide occur in an anti configuration without rotation, so this process results in a trans- (E-) allyl alcohol.

The purported mechanism for these reactions is shown in equations 4 and 5.

EQUATION 4

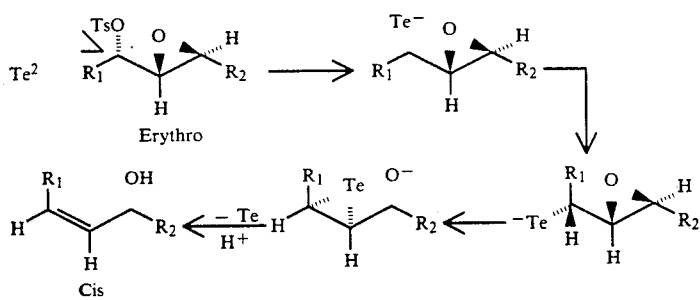

EQUATION 5

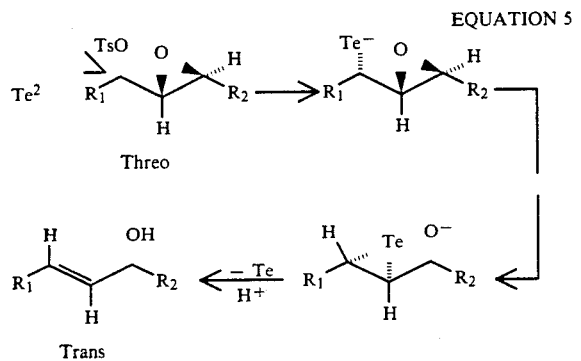

A number of erythro and threo epoxides were tested in which the $R_1$ and $R_2$ substituents were as shown in the table below. All show excellent purity and high yield. In the last example (c-$C_6H_{11}$), the tellurium reduction was with lithium triethyl borohydride (LiEt$_3$BH) in THF (tetrahydrofuran). In all other cases, the treatment involved NaBH$_4$.

TABLE I

| THREO- | | TRANS (E) | |
| --- | --- | --- | --- |
| $R_1$ | $R_2$ | E/Z Ratio | Yield |
| Me | n-$C_5H_{11}$ | >50:1 | 91% |
| H$_2$C⌒CH$_2$ | Me | >50:1 | 91% |
| c-$C_6H_{11}$ | Me | >50:1 | 83% |
| H | n-Pr | — | 95% |

TABLE II

| ERYTHRO | | CIS (Z) | |
| --- | --- | --- | --- |
| $R_1$ | $R_2$ | Z/E Ratio | Yield |
| Me | n-$C_5H_{11}$ | >50:1 | 84% |
| H$_2$C⌒CH$_2$ | Me | >50:1 | 88% |
| c-$C_6H_{11}$ | Me | >50:1 | 81% |
| n-Pr | n-Pr | >50:1 | 56% |
| n-$C_6H_{13}$ | Et | >50:1 | 80% |
| c-$C_6H_{11}$ | c-$C_6H_{11}$ | 15:1 | 94% |

>50:1 indicates that the minor isomer could not be detected by $^1$H NMR

The assignment of the erythro and threo stereochemistry was determined by $^1$H and $^{13}$C NMR and by comparison with authentic erythro-glycidols which are obtained nearly exclusively in the Sharpless kinetic resolution of secondary allyl alcohols. The cis- or trans-olefin assignments also were determined by $^1$H and $^{13}$C NMR and also by inspection of the infrared spectrum. Generally, in the $^1$H NMR spectrum the methine proton of the carbinol center of the trans-compounds are shifted 0.5 PPM downfield from the absorption of the cis-compound. The infrared spectrum of disubstituted trans-compounds usually shows a variably intense absorption at 1678-1668 cm$^{-1}$ and a strong absorption at 980-960 cm$^{-1}$. For cis-disubstituted compounds, the absorptions are generally at 1662-1626 cm$^{-1}$ and 730-665 cm$^{-1}$. In this process a unique reducing system and solvent system is employed. Tellurium is reduced by action of two molar equivalents of sodium borohydride in dimethylformamide (DMF) to give sodium telluride (Na$_2$Te), diborane (B$_2$H$_6$), and hydrogen gas (H$_2$),

EQUATION 6

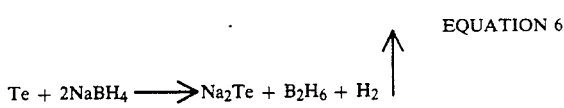

or is reduced by action of lithium triethyl borohydride in THF.

DMF is an excellent solvent for stabilizing ionic intermediates. DMF has a relatively low vapor pressure and a boiling point of 140°. Thus, reactions can be run at elevated temperatures (typically 50°-70° C.).

When glycidyl mesylates which are not terminal epoxides are subjected to treatment of telluride ion in DMF, the attack of telluride ion on the epoxide is not observed. Rather, the only observed organic product is one which results from the attack of the telluride ion to displace the sulfonate. When a 1:1 mixture of erythro-/threo diastereomers of a glycidyl sulfonate is treated with telluride ion, a 1:1 mixture of cis-and trans-allyl alcohols results as the only observed organic product.

If a poorer leaving group is substituted for the sulfonate leaving group, the preference for tellurium attack switches to the epoxide.

Either of the two above systems will act readily on an internal epoxide, i.e., an epoxide that does not involve a terminal carbon. This permits the racemic mixture to be separated into the two pure enantiomers, e.g. by employing SKR followed by tosylation of the epoxy alcohol and telluride reaction of the glycidyl tosylate, the double bond and the alcohol functions are transposed. The process can be used to obtain a desired cis or trans compound, i.e., one having a desired relative stereochemistry to produce an effective biological or agricultural agent.

This process permits recovery and recycling of the tellurium. The Te/DMF system is not especially toxic, and no unusual health or safety precautions are required. Other systems besides Na$_2$Te in DMF can be employed. Selenium will produce acceptable results in many cases, but can also produce a selenocyclobutane; tellurium does not produce an analogous tellurocyclobutane. As mentioned in the examples, the system can include LiEt₃BH.

While this invention has been described in detail with reference to several examples of preferred embodiments, the invention is not limited to those precise embodiments, and many modifications and variations will present themselves to those of skill in the art without departing from the scope and spirit of this invention, as defined in the appended claims.

What is claimed is:

1. A process of converting an erythro epoxy alcohol of the general form

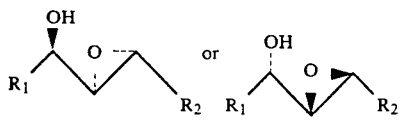

to a substantially pure cis-allyl alcohol of the form

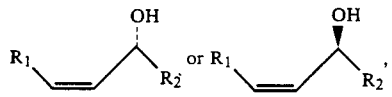

respectively where R₁ is hydrogen, normal lower alkyl, allyl, or cyclohexyl and R₂ is normal lower alkyl or cyclohexyl; comprising the steps of
introducing toluenesulfonic anhydride in a suitable carrier into said erythro epoxy alcohol to form an epoxy tosylate; and
contacting the epoxy tosylate with a salt of an element selected from the group that consists of Te and Se to form said cis-allyl alcohol.

2. The process of claim 1 wherein said salt is a telluride.

3. The process of claim 1 wherein said suitable carrier for the toluenesulfonic anhydride includes methylene chloride.

4. The process of claim 1 further comprising preparing said salt by adding elemental tellurium and a salt of a borohydride to dimethylformamide.

5. A process of converting a threo epoxy alcohol of the form

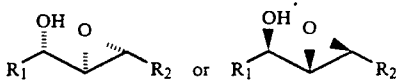

to a substantially pure trans-allyl alcohol of the form

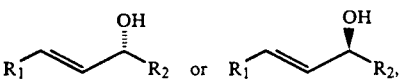

respectively where R₁ is hydrogen, normal lower alkyl, allyl, or cyclohexyl and R₂ is normal lower alkyl or cyclohexyl; comprising the steps of
introducing a toluenesulfonic anhydride in a suitable carrier into said threo epoxy alcohol to form an epoxy tosylate; and
contacting the epoxy tosylate with a salt of an element selected from the group that consists of Te and Se to form said trans allyl alcohol.

6. The process of claim 5 wherein said salt is a telluride.

7. The process of claim 5 wherein said suitable carrier for the toluenesulfonic anhydride includes methylene chloride.

8. The process of claim 5 further comprising preparing said salt by adding elemental tellurium and a salt of a borohydride to dimethylformamide.

* * * * *